US00RE47883E

(19) United States
(12) Reissued Patent
Lark et al.

(10) Patent Number: US RE47,883 E
(45) Date of Reissued Patent: Mar. 3, 2020

(54) ULTRASONIC BLADE WITH STATIC CASING

(71) Applicants: Robert K. Lark, Chapel Hill, NC (US); Edward C. Skolnick, Wharton, NJ (US); Antoine Kaeslin, Norwalk, CT (US); Pranli K. Tambe, San Diego, CA (US)

(72) Inventors: Robert K. Lark, Chapel Hill, NC (US); Edward C. Skolnick, Wharton, NJ (US); Antoine Kaeslin, Norwalk, CT (US); Pranli K. Tambe, San Diego, CA (US)

(21) Appl. No.: 15/792,941

(22) Filed: Oct. 25, 2017

Related U.S. Patent Documents

Reissue of:
(64) Patent No.: 9,554,809
Issued: Jan. 31, 2017
Appl. No.: 14/700,189
Filed: Apr. 30, 2015

U.S. Applications:
(60) Provisional application No. 62/057,369, filed on Sep. 30, 2014.

(51) Int. Cl.
*A61B 17/32* (2006.01)
*A61B 17/16* (2006.01)

(52) U.S. Cl.
CPC .. *A61B 17/1613* (2013.01); *A61B 17/320068* (2013.01); *A61B 2017/320088* (2013.01)

(58) Field of Classification Search
CPC ..... A61B 17/32008; A61B 17/320068; A61B 17/320088; A61B 2017/1651; A61B 2017/1653; A61C 3/03
USPC ..... 606/169, 167
See application file for complete search history.

(56) References Cited

U.S. PATENT DOCUMENTS

| | | | | |
|---|---|---|---|---|
| 1,368,842 | A | 2/1921 | Roeling | |
| 3,805,787 | A | 4/1974 | Banko | |
| 4,008,720 | A | 2/1977 | Brinckmann | |
| 4,491,132 | A | 1/1985 | Aikins | |
| 5,087,261 | A | 2/1992 | Ryd et al. | |
| 5,122,142 | A | 6/1992 | Pascaloff | |
| 5,188,102 | A | 2/1993 | Idemoto | |
| 5,248,296 | A | 9/1993 | Alliger | |
| 5,261,922 | A | 11/1993 | Hood ..... | A61B 17/32006 30/355 |

(Continued)

*Primary Examiner* — Cary E Wehner
(74) *Attorney, Agent, or Firm* — Law Office of Robert M. White, PLLC

(57) ABSTRACT

An ultrasonic surgical device capable of cutting biological tissues such as bone and cartilage. The ultrasonic surgical device includes a static casing, which sheaths an ultrasonic horn, and a lubrication film, which separates the ultrasonic horn and the static casing. The static casing, which also incorporates a plurality of fluid channels to allow passage of fluids along its length and eventual distribution of such fluids at the cutting end and biological tissue interface, inhibits the transfer of heat generated along the ultrasonic horn. The cutting end and the static casing are separated by a flexible joint, which serves to inhibit the transfer of vibrational energy, and consequently heat, from the cutting end to the static casing. As such, the static casing remains stable and can be used both to manipulate the surgical device with greater haptic control and facilitate effective penetration of larger cross-sections of biological tissue.

6 Claims, 9 Drawing Sheets

(56) References Cited

U.S. PATENT DOCUMENTS

| | | | | |
|---|---|---|---|---|
| 5,318,570 | A | 6/1994 | Hood | |
| 5,322,055 | A | 6/1994 | Davison | |
| 5,346,502 | A | 9/1994 | Estabrook | |
| 5,624,393 | A | 4/1997 | Diamond | |
| 5,989,275 | A | 11/1999 | Estabrook | |
| 6,033,375 | A | 3/2000 | Brumbach | |
| 6,224,565 | B1 * | 5/2001 | Cimino | A61B 17/32006 604/163 |
| 6,379,371 | B1 | 4/2002 | Novak | A61B 17/32006 30/123.3 |
| 6,443,969 | B1 | 9/2002 | Novak | A61B 17/32006 606/169 |
| 8,343,178 | B2 | 1/2013 | Novak | A61B 17/32006 606/169 |
| 8,348,880 | B2 | 1/2013 | Messerly | |
| 8,628,534 | B2 | 1/2014 | Jones | |
| 9,095,367 | B2 * | 8/2015 | Olson | A61B 17/32006 |
| 2012/0172786 | A1 * | 7/2012 | MacKool | A61F 9/00745 604/22 |
| 2017/0112524 | A1 * | 4/2017 | Smith | A61B 17/32006 |

* cited by examiner

ULTRASONIC BLADE WITH STATIC CASING

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCES TO RELATED APPLICATION

This application claims the benefit of provisional patent application Ser. No. 62/057,369, filed Sep. 30, 2014 on behalf of the present inventors.

STATEMENT REGARDING ADDITION OF NEW MATTER

This is a substitute specification made in response to the Notice to File Corrected Application Papers mailed on Nov. 4, 2016. This substitute specification does not include new matter. Page number requirements (37 CFR 1.52(b)(5)) were not adhered to for the specification as originally filed, but this substitute specification is corrected with respect to those requirements.

STATEMENT REGARDING FEDERALLY SPONSORED RESEARCH OR DEVELOPMENT

Not applicable.

REFERENCE TO SEQUENCE LISTING, A TABLE, OR A COMPUTER PROGRAM LISTING COMPACT DISK APPENDIX

Not Applicable.

BACKGROUND OF INVENTION

1. Field of Invention

The present invention relates to the field of ultrasonic surgical devices capable of cutting biological tissues such as bone and cartilage.

2. Description of Related Art

Traditional surgical saws, such as oscillating saws and reciprocating saws, allow users to cut bones (i.e. Perform osteotomies) of relatively large diameters, such as the tibia and femur. These types of surgical saws, however, which are similar in many ways to the toothed saws used to cut wood, metal, and plastic, have significant disadvantages with respect to a patient's well-being. Because surgical saws utilize rapid motion of the saw blade to cut biological tissues, such as bone and cartilage, a significant amount of heat is generated along the blade and particularly at the blade and bone interface. This can be harmful to the patient since prolonged exposure of bone cells to temperatures at or in excess of 47° C. leads to necrosis of those osteocytes. Another disadvantage of these oscillating and reciprocating bone saws is that they produce uneven cuts, preventing ideal realignment and reduction of the osteotomy gap, which is detrimental to efficient healing of the bone. Oscillating and, in particular, reciprocating bone saws, which utilize a number of sharpened teeth along their cutting edges, can tear neighboring soft tissues that are inadvertently caught in the serrations of the rapidly moving blade. Tearing of these soft tissues leads to significant blood loss and potential nerve damage, which undoubtedly hampers the health of the patient.

Traditional oscillating and reciprocating bone saws have employed a variety of different measures to address these disadvantages. With respect to the generation of excessive heat, these surgical saws can utilize irrigation systems to flush the surgical site near the blade and bone interface. These irrigation systems can be separate, requiring an additional device at the surgical site, or integrated. Although effective at flushing a surgical site of unwanted sources of added friction, these irrigation systems are relatively ineffective at actually cooling the blade at the blade and bone interface. For example, one design for a surgical saw that incorporates a means for irrigation comprises a channel between otherwise parallel portions of a saw blade through which fluid can flow out into the surgical site (U.S. Pat. No. 5,087,261). This channel, though, can be easily compacted with surgical debris, rendering the integrated irrigation system unusable. In addition, providing a channel between parallel portions of the saw blade necessarily increases the likelihood of a wider, more uneven cut. Other designs for an oscillating bone saw include outlets along the blade's edge to facilitate irrigation along the blade and bone interface (U.S. Pat. No. 4,008,720; U.S. Pat. No. 5,122,142). However, these channels can be similarly compacted with surgical debris, rendering them useless. More so, channels along the very blade edge result in a blade edge that is not continuous, which reduces the cutting efficiency of the blade. Despite any potential efficacy in flushing a site of surgical debris, these systems do very little to actually cool the very blade edge, specifically at the blade and bone interface.

Just as with saws used to cut wood, metal, and plastic, a user can avoid rough or uneven cuts by using a saw blade that incorporates more teeth along the edge of the blade and/or teeth having differing angles. While this can produce a relatively finer cut, the resulting cut still leaves much to be desired in terms of producing smooth, even bone surfaces. Cutting guides, which help to stabilize the blade and keep it on a prescribed plane, are often utilized during an osteotomy to improve the precision of the cut. Still, the improvement is not substantial enough to consider these measures a long-term solution with respect to producing smooth bone cuts. In fact, adding teeth or guiding the blade edge have little effect in preventing inadvertent tearing of neighboring soft tissues. Although efforts are taken to protect soft tissues from damage and prevent significant blood loss, the inherently close confines typical in performing any osteotomy make it extremely difficult to completely eliminate such damage, especially to those tissues that are unseen or positioned beneath the bone being cut. This is compounded by the fact that the saw blades used with many oscillating and reciprocating bone saws are relatively large.

A variety of ultrasonic surgical devices are now utilized in a number of surgical procedures, including surgical blades that are capable of cutting biological tissues such as bone and cartilage. These types of saw blades are powered by high-frequency and high-amplitude sound waves, consequent vibrational energy being concentrated at the blade's edge by way of an ultrasonic horn. Being powered by sound waves, neighboring soft tissues are not damaged by these types of blades because the blade's edge effectively rebounds due to the elasticity of the soft tissue. Thus, the significant blood loss common with use of traditional bone saws is prevented. In addition, significantly more precise cuts are possible using ultrasonic bone cutting devices, in part, because the blade's edge does not require serrations. Instead, a continuous and sharpened edge, similar to that of a typical scalpel, enables a user to better manipulate the surgical device without the deflection caused by serrations, which is common when using oscillating and reciprocating bone saws. Although ultrasonic cutting blades are advantageous in that they are less likely to tear neighboring soft tissues and more likely to produce relatively more even cuts, these types of blades still generate considerable amounts of heat.

As with traditional bone saws, separate or integrated irrigation systems are often utilized in order to flush the surgical site and generally provide some measure of cooling effect to the blade. However, many of these blades suffer from the same disadvantages as traditional bone saws that have tried to incorporate similar measures. For example, providing openings along the blade's edge through which fluid flows introduces voids in the cutting edge, thereby inhibiting the cutting efficiency of the blade (U.S. Pat. No. 5,188,102). In addition, these fluid openings can be readily compacted with surgical debris, rendering them useless for their intended function. In other blade designs, the continuity of the blade is maintained and a fluid outlet is positioned just before the blade's edge (U.S. Pat. No. 8,348,880). However, this fluid outlet merely irrigates the surgical site since it is positioned too far from the blade and bone interface to actually provide the necessary cooling effect. Also, it irrigates only one side of the blade. Another design for an ultrasonic cutting device, which claims to cool the blade, incorporates an irrigation output located centrally along the longitudinal axis of the blade (U.S. Pat. No. 6,379,371). A recess in the center of the blade tip allows fluid to flow out of this output and toward the blade's edge, flow that is propelled by a source of pressure. However, the positioning of this irrigation output within the contour of the blade tip results in a bifurcation or splitting of the irrigation flow, such splitting tending to distribute fluid at an angle away from the blade's edge. Mentioned above, the excessive heat generated using any cutting blade, including an ultrasonic cutting blade, is focused most significantly at the blade and bone interface. This example for an ultrasonic blade with cooling capabilities, then, does little to actually cool the blade at the blade and bone interface, but instead serves merely to flush debris from the surgical site. Furthermore, this ultrasonic blade is not well-suited to cutting large cross-sections of bone and is used almost exclusively in oral or maxillofacial surgeries, which involve cutting of small bones.

Even assuming that any of the irrigation systems incorporated into the various bone saws provide some measure of cooling, thermal burning of both neighboring soft tissues and bone surfaces remains a significant problem. Because the shaft of the blade also vibrates at a very high frequency, considerable heat is generated along its length, too. The vibrating shaft contacts neighboring soft tissues, potentially burning them. With respect to an osteotomy, as the blade passes through the cross-section of bone, the freshly-cut bone surfaces remain in constant and direct contact with the rapidly vibrating shaft of the blade. As a result, it is not uncommon to burn the bone, produce smoke and, more importantly, kill osteocytes. In fact, simply lengthening an ultrasonic blade to accommodate large cross-sections of bone tissue, for example, increases the surface area through which heat can transfer and, thus, is avoided by manufacturers of these types of blades. While irrigation directed specifically toward the blade's leading edge may provide some measure of cooling at the blade and bone interface, irrigation alone is insufficient in trying to avoid prolonged exposure of bone tissue, for example, to temperatures in excess of 47° C. Therefore, there remains a need for an ultrasonic surgical device that is capable of cutting bones with large cross-sections, such as the femur, while maintaining a working temperature along the entirety of the blade shaft that does not inhibit proper healing of the bone tissue.

BRIEF SUMMARY OF INVENTION

According to one embodiment, an ultrasonic surgical device capable of cutting, ablating, abrading or otherwise transforming biological tissues comprises a housing, at least one ultrasonic horn, a static casing, a flexible joint, and a cutting end. The housing contains components, such as a piezoelectric transducer and transducer backing material, known in the art to generate and propagate ultrasonic vibrations along the ultrasonic horn toward the cutting end. The static casing, which comprises at least one sheathing slot, sheaths at least a portion of the ultrasonic horn. In addition, the sheathing slot is separated from the ultrasonic horn by at least one lubrication film. As a result, the static casing has the advantage of reducing both the generation of heat due to movement of the ultrasonic horn and subsequent transfer of such heat to neighboring biological tissues. In addition, the static casing has the added benefit of providing a user with greater haptic control during a surgical procedure as the user can directly manipulate the ultrasonic horn by way of the static casing. Not only does the static casing offer greater sensitivity but it enables a user to penetrate a much larger cross-section of biological tissues without damaging adjacent tissues due to excessive heat transfer.

The static casing, according to another embodiment, further comprises a plurality of fluid channels that extend the length of the static casing and can be utilized to dispense a variety of fluids, including therapeutic agents and saline, to the surgical site. Fluid flowing along these channels is discharged at the cutting end and biological tissue interface, where it serves, in part, to both limit heat transfer at the interface and irrigate the surgical site. Not only does this fluid serve to cool this interface and irrigate the site but it also cools the static casing as it flows along these fluid channels. As a result, these fluid channels are advantageous in further reducing the transfer of heat generated along the main body of the ultrasonic horn to the static casing, thereby reducing any likelihood of damage to adjacent tissues that are in contact with the static casing. This is especially beneficial as the cutting end penetrates deeper into large bones, for example.

The static casing has a width and height profile similar to the cutting end, which enables deeper penetration of the cutting end, and is separated from the cutting end by a flexible joint. This flexible joint, preferably composed of a viscoelastic material, surrounds at least a portion of the ultrasonic horn and reduces the transfer of vibrational energy from the cutting end to the static casing. This separation helps to preserve the immobility and stability of the static casing. According to at least one embodiment, the flexible joint further comprises a plurality of through-ports which facilitate continuous fluid flow from the fluid channels, through the flexible joint, and to the cutting end. At least one embodiment comprises a cutting end having openings through which fluid, that is delivered along the fluid channels of the static casing and through the through-ports of the flexible joint, is discharged toward the blade and bone interface.

REFERENCE NUMERALS FOR DRAWINGS

Please Note that First Digit Indicates the Figure in which a Component is First Visually-Identifiable

| | |
|---|---|
| 110 | Ultrasonic surgical device |
| 112 | Housing |
| 114 | Static casing |
| 116 | Ultrasonic horn |
| 118 | Flexible joint |
| 120 | Cutting end |
| 126 | Sheathing slot |
| 128 | Lubrication film |
| 130 | Fluid channel |
| 132 | Longitudinal edge |
| 136 | Channel insert |
| 138 | Inlet comlector |
| 140 | Discharge orifice |
| 142 | Passage |
| 144 | Attachment end |
| 148 | Top planar surface |
| 150 | Opening |
| 152 | Blade edge |
| 156 | Sloped top surface |
| 158 | Interior edge |
| 310 | Static casing |
| 312 | Sheathing slot |
| 314 | Fluid channel |
| 316 | Ultrasonic horn |
| 318 | Lubrication film |
| 320 | Longitudinal edge |
| 410 | Cutting end assembly |
| 434 | Through-port |
| 454 | Bottom planar surface |
| 460 | Sloped bottom surface |
| 462 | Inlet |
| 510 | Ultrasonic surgical device |
| 512 | Housing |
| 514 | Static casing |
| 516 | Ultrasonic horn |

-continued

| | |
|---|---|
| 518 | Flexible joint |
| 520 | Cutting end |
| 526 | Sheathing slot |
| 528 | Lubrication film |
| 530 | Fluid channel |
| 532 | Longitudinal edge |
| 536 | Channel insert |
| 538 | Inlet comlector |
| 540 | Discharge orifice |
| 542 | Passage |
| 544 | Attachment end |
| 548 | Top planar surface |
| 550 | Opening |
| 552 | Blade edge |
| 556 | Sloped top surface |
| 558 | Interior edge |
| 610 | Cutting end assembly |
| 634 | Through-port |
| 654 | Bottom planar surface |
| 660 | Sloped bottom surface |
| 662 | Inlet |
| 710 | Ultrasonic surgical device |
| 712 | Housing |
| 714 | Static casing |
| 716 | Ultrasonic horn |
| 718 | Flexible joint |
| 720 | Cutting end |
| 726 | Sheathing slot |
| 728 | Lubrication film |
| 730 | Fluid channel |
| 732 | Longitudinal edge |
| 736 | Channel insert |
| 738 | Inlet comlector |
| 740 | Discharge orifice |
| 742 | Passage |
| 744 | Attachment end |
| 748 | Top planar surface |
| 752 | Blade edge |
| 764 | Blade teeth |
| 810 | Cutting end assembly |
| 834 | Through-port |
| 854 | Bottom planar surface |
| 862 | Inlet |
| 910 | Ultrasonic surgical device |
| 912 | Housing |
| 914 | Static casing |
| 916 | Ultrasonic horn |
| 918 | Flexible joint |
| 920 | Cutting end |
| 926 | Sheathing slot |
| 928 | Lubrication film |
| 932 | Longitudinal edge |
| 942 | Passage |
| 944 | Attachment end |
| 948 | Top planar surface |
| 952 | Blade edge |

DETAILED DESCRIPTION OF DRAWINGS

Figure 1:
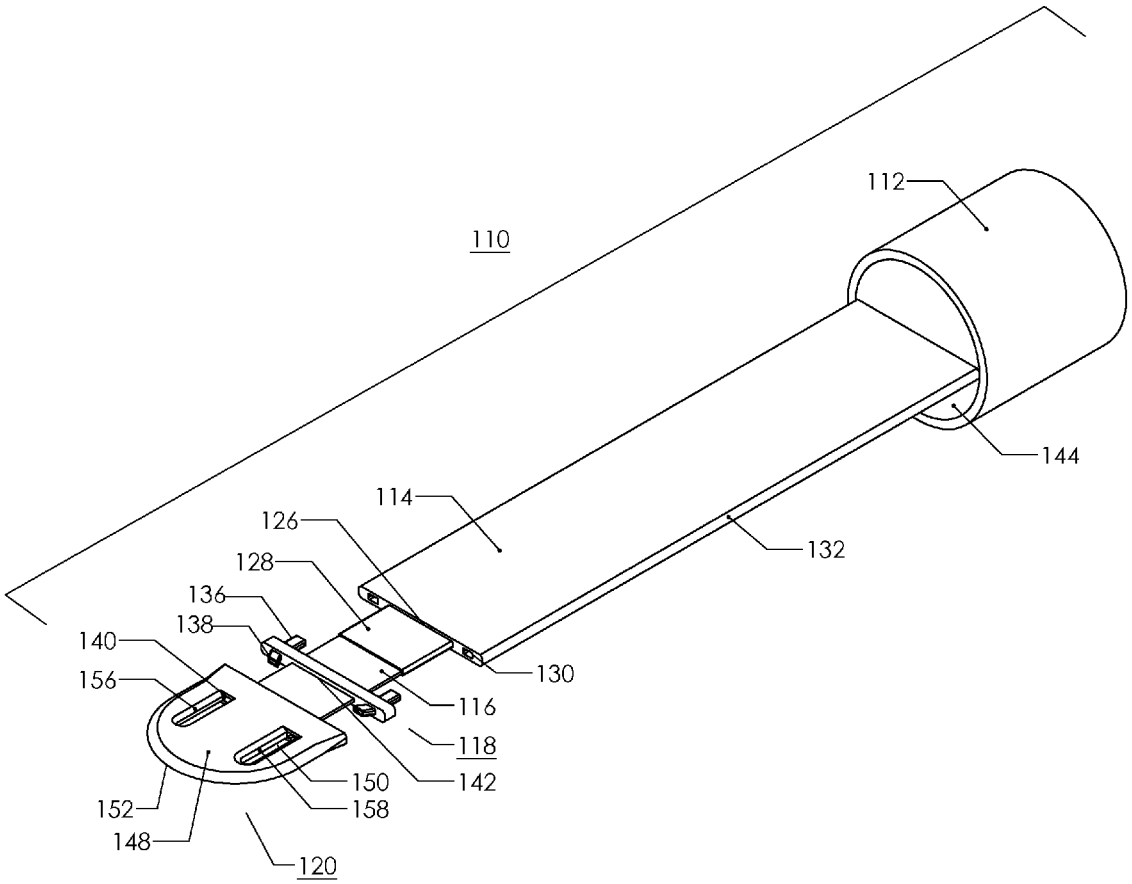
FIG. 1 is an exploded perspective view indicating many components of one embodiment.

FIG. 1 shows an exploded perspective view of one embodiment of an ultrasonic surgical device 110. The ultrasonic surgical device 110 comprises a housing 112, a static casing 114, at least one ultrasonic horn 116, a flexible joint 118, and a cutting end 120. The housing 112 contains components, such as a piezoelectric transducer and a transducer backing material, known to those skilled in the art to be related to the generation and propagation of ultrasonic vibrations to the cutting end 120. The piezoelectric transducer, which produces ultrasonic vibrations, is operatively coupled to a first end of the ultrasonic horn 116. Ultrasonic vibrations propagate along a main body of the ultrasonic horn 116 toward a second end of the ultrasonic horn 116, the second end being coupled to the cutting end 120. The static casing 114 sheaths the ultrasonic horn 116, the ultrasonic horn 116 being preferably positioned within a sheathing slot 126 located preferably along the central longitudinal axis of the static casing 114. The sheathing slot 126 and the ultrasonic horn 116 are separated from one another by at least one lubrication film 128. The lubrication film 12R reduces transfer of vibrational energy from the ultrasonic horn 116 and, thus, heat to the static casing 114. The static casing 114 and the cutting end 120 are separated by the flexible joint 118, which reduces the transfer of vibrational energy from the cutting end 120 to the static casing 114.

The static casing 114 comprises an attachment end 144 and an opposite end, the attachment end 144 adapted for coupling to the housing 112. The static casing 114 further comprises a plurality of fluid channels 130 which extend the length of the static casing 114. These fluid channels 130 allow fluid to flow through the static casing 114. A plurality of longitudinal edges 132 further define the static casing 114, these longitudinal edges 132 being preferably rounded or filleted. The flexible joint 118 is characterized in part by a plurality of through-ports 434 and at least one passage 142. The through-ports 434 are better visualized in FIG. 4. The passage 142, which is substantially aligned with the sheathing slot, allows at least a portion of the ultrasonic horn 116 to pass through the flexible joint 118.

Each through-port 434 comprises a channel insert 136 and an inlet connector 138. The cutting end 120 comprises a plurality of inlets 462 and a plurality of discharge orifices 140. The inlets 462 are better visualized in FIG. 4. Each channel insert 136 communicates with one of the fluid channels 130 of the static casing 114. Each inlet connector 138 communicates with one of the inlets 462 and each inlet 462 communicates with one of the discharge orifices 140. Communication between the fluid channel 130, channel insert 136, through-port 434, inlet connector 138 and inlet 462 allows fluid to flow continuously from the fluid channel 130, through the through-port 434, and into the cutting end 120, where the fluid is subsequently discharged at, for example, the cutting end 120 and biological tissue interface by way of the discharge orifice 140. It is preferred that the flexible joint 118 comprise both the channel inserts 136 and the inlet connectors 138 in order to facilitate continuous fluid flow. However, it should be noted that the flexible joint 118 can comprise channel inserts 136 but not inlet connectors 138, inlet connectors 138 but not channel inserts 136, or neither channel inserts 136 nor inlet connectors 138.

The cutting end 120 can be a blade tip adapted to cutting, ablating, abrading or otherwise transforming, for example, bone tissue. The cutting end 120 comprises a top planar surface 148 and a bottom planar surface 454, the top planar surface 148 and bottom planar surface 454 defined by a plurality of openings 150. The bottom planar surface 454 is better visualized in FIG. 4. Each opening 150 extends through the depth of the cutting end 120 from the top planar surface 148 to the bottom planar surface 454 and communicates with at least one of the discharge orifices 140. Each opening 150 is substantially circular and each is characterized in part by a sloped top surface 156 originating from an interior edge 158 situated approximately along the median horizontal plane of the cutting end 120. The sloped top surface 156 slopes up from the interior edge 158 and toward the top planar surface 148. Better visualized in FIG. 4, each opening 150 is further characterized by a sloped bottom surface 460, which originates from the interior edge 158 situated approximately along the median horizontal plane of the cutting end 120. The sloped bottom surface 460 slopes down from the interior edge 158 and toward the bottom planar surface 454. The cutting end 120 further includes at least one blade edge 152, the blade edge 152 in this embodiment preferably being a continuous, planar arc, and sharpened along its entirety. It should be noted, however, that the blade edge 152 can be adapted to have serrations or any other type of edge suitable for cutting, ablating, abrading or otherwise transforming, for example, bone tissue.

As shown, the longitudinal edges 132 of the static casing 114 are preferably filleted or substantially rounded. The static casing 114 is preferably made of a material suitable for biomedical applications, such as titanium, stainless steel, PEEK, PE, or PTFE. Optionally, the outer surface of the static casing 114 may be coated with a lubricant, such as a solid film or a fluid film. Similarly, the cutting end 120 is preferably made of a material suitable for biomedical applications, such as titanium, stainless steel, PEEK, PE, or PTFE. Optionally, the cutting end 120 may be coated with a lubricant, such as a solid film or a fluid film. The ultrasonic horn 116, too, is preferably made of a material suitable for biomedical applications, such as titanium, stainless steel, PEEK, PE, or PTFE. The lubrication film 128, which is preferably adhered to the ultrasonic horn 116, is preferably a solid film lubricant. The lubrication film 128 may also be made of a hydrodynamic lubricant or any other lubricant suitable for the application. Alternatively, the sheathing slot 126 may be coated with a lubrication film 128, such lubrication film 128 being a solid film lubricant, hydrodynamic lubricant, or any other lubricant suitable for the application. It should be noted that both the sheathing slot 126 and the ultrasonic horn 116 may be coated with the lubrication film 128. The flexible joint 118 is preferably made of a viscoelastic material, such as silicone.

Ultrasonic vibrations are produced by the piezoelectric transducer and are transferred to the ultrasonic horn 116, which concentrates or amplifies these vibrations at the cutting end 120. Movement of the cutting end 120 generates heat, which can be detrimental to biological tissues that come in contact with the cutting end 120. Fluid, which may be a coolant such as saline, flows through the fluid channels 130 and exits the discharge orifices 140, where it is distributed at the cutting end 120 and biological tissue interface. Such fluid inhibits the generation of heat at this interface, thereby reducing the likelihood of damage to the tissue. In addition, fluid flowing through the fluid channels 130 actively cools the static casing 114. Fluid flowing along these fluid channels 130 may also incorporate therapeutic agents, such as bone morphogenetic protein 2, transforming growth factor B1 protein, or fibroblast growth factor 2 protein. In fact, one fluid channel can be dedicated to supplying irrigation, such as saline, while another fluid channel can be dedicated to administration of therapeutic agents.

Not only is heat generated at the cutting end 120 but it is also generated along the length of the ultrasonic horn 116. The static casing 114, therefore, inhibits the transfer of heat generated along the ultrasonic horn 116 to neighboring tissues. In addition, the static casing 114 offers the user a stable means of manipulating the surgical device 110 with greater sensitivity. The ultrasonic horn 116 is separated from the sheathing slot 126 by the lubrication film 128 in order to reduce friction caused by vibrational energy between the ultrasonic horn 116 and the sheathing slot 126. The flexible joint 118 separates the cutting end 120 from the static casing 114 and inhibits the transfer of vibrational energy from the cutting end 120 to the static casing 114. The flexible joint 118 and the lubrication film 128 work in conjunction to inhibit transfer of vibrational energy, and thus heat, to the static casing 120. The static casing 114, having substantially the same width and height profile as the cutting end 120, allows for deeper and more sensitive penetration of the surgical device 110 without the attendant heat typically generated, which results from vibrational energy and frictional forces, along the shaft of an ultrasonic cutting device.

Figure 2:
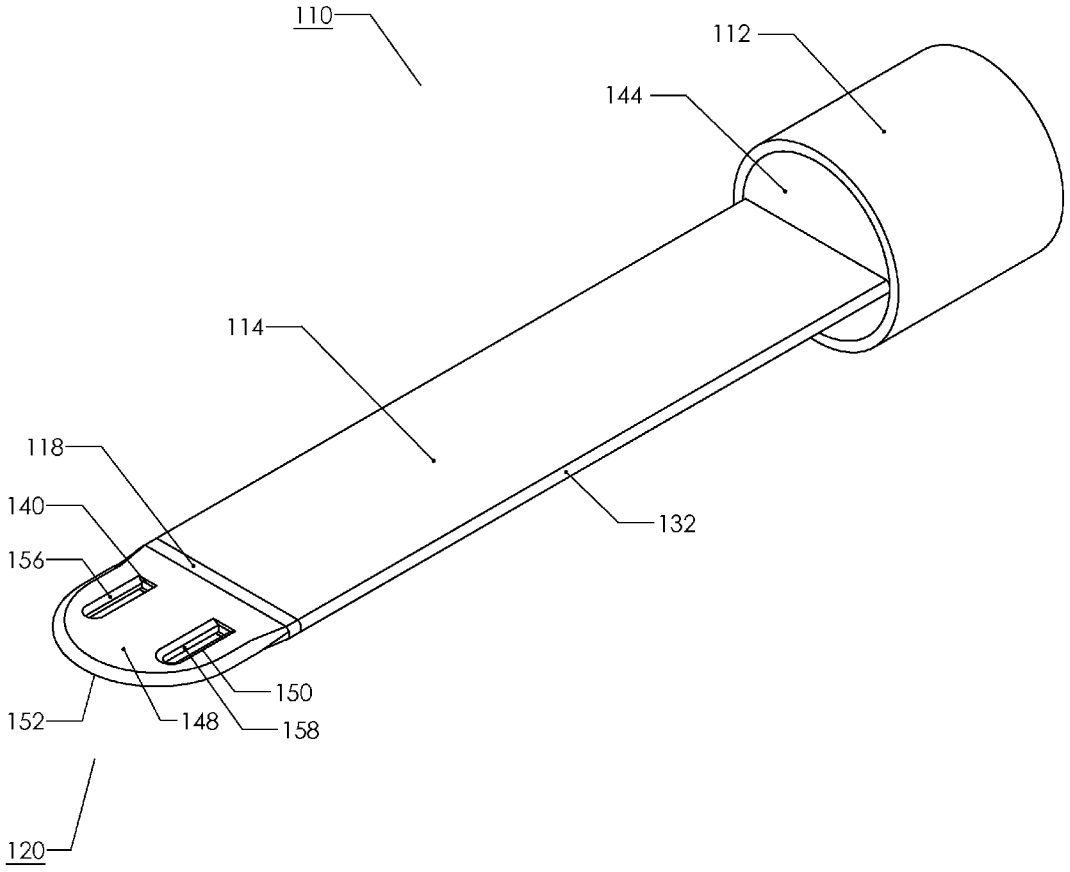
FIG. 2 is a perspective view showing an assembled example of one embodiment.

FIG. 2 is a perspective view of one embodiment in an assembled state. An ultrasonic surgical device 110 comprises a housing 112, a static casing 114, a flexible joint 118, and a cutting end 120. The housing 112 contains components, such as a piezoelectric transducer and a transducer backing material, known to those skilled in the art to be related to the generation and propagation of ultrasonic vibrations to the cutting end 120. The static casing 114 sheaths an ultrasonic horn, the ultrasonic horn 116 being preferably positioned within a sheathing slot located preferably along the central longitudinal axis of the static casing 114. The ultrasonic horn and the sheathing slot are better visualized in FIG. 1. The static casing 114 comprises an attachment end 144 and an opposite end, the attachment end 144 adapted for coupling to the housing 112. A plurality of longitudinal edges 132 further define the static casing 114, these longitudinal edges 132 being preferably rounded or filleted. The opposite end is separated from the cutting end 120 by the flexible joint 118.

The cutting end 120 can be a blade tip adapted to cutting, ablating, abrading or otherwise transforming, for example, bone tissue. The cutting end 120 comprises a top planar surface 148 and a bottom planar surface 454, the top planar surface 148 and bottom planar surface 454 defined by a plurality of openings 150. The bottom planar surface 454 is better visualized in FIG. 4. Each opening 150 extends through the depth of the cutting end 120 from the top planar surface 148 to the bottom planar surface 454 and communicates with at least one of a plurality of discharge orifices 140. Each opening 150 is substantially circular and each opening 150 is characterized in part by a sloped top surface 156 originating from an interior edge 158 situated approximately along the median horizontal plane of the cutting end 120. The sloped top surface 156 slopes up from the interior edge 158 and toward the top planar surface 148. Better visualized in FIG. 4, each opening 150 is further characterized by a sloped bottom surface 460, which originates from the interior edge 158 situated approximately along the median horizontal plane of the cutting end 120. The sloped bottom surface 460 slopes down from the interior edge 158 and toward the bottom planar surface 454. The cutting end 120 further includes at least one blade edge 152, the blade edge 152 in this embodiment preferably being a continuous, planar arc, and sharpened along its entirety. It should be noted, however, that the blade edge 152 can be adapted to have serrations or any other type of edge suitable for cutting, ablating, abrading or otherwise transforming, for example, bone tissue.

Figure 3:
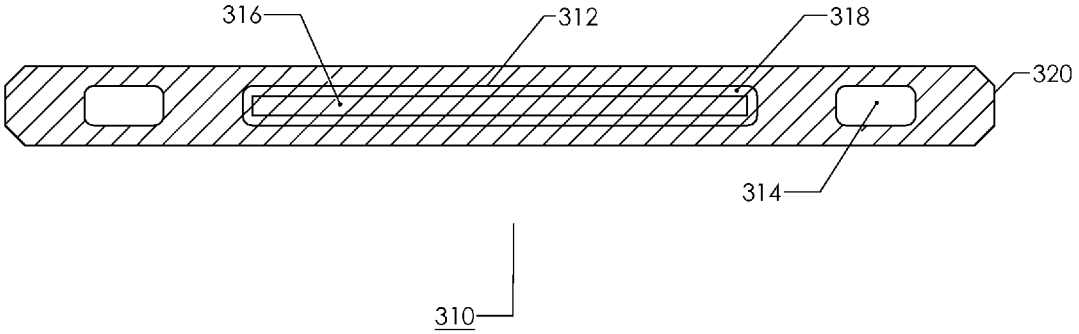
FIG. 3 is a cross-section view of one embodiment showing a static casing sheathing an ultrasonic horn with a lubrication film separating the static casing from the ultrasonic horn.

FIG. 3 is a cross-sectional view of one embodiment, a view illustrating components of a static casing 310. The static casing 310 comprises at least one sheathing slot 312 and a plurality of fluid channels 314. There is at least one ultrasonic horn 316, the ultrasonic horn being sheathed by the sheathing slot 312, the sheathing slot 312 being located preferably along the central longitudinal axis of the static casing 310. The ultrasonic horn 316 is separated from the sheathing slot 312 by at least one lubrication film 318. The static casing 310 is further defined by a plurality of longitudinal edges 320, the longitudinal edges 320 being preferably filleted or rounded.

The lubrication film 318, which is preferably a solid film lubricant, can coat the outer surface of the ultrasonic horn 316, the inner surface of the sheathing slot 312, or both the outer surface of the ultrasonic horn 316 and the inner surface of the sheathing slot 312. The lubrication film 318 may also be a hydrodynamic lubricant or any other lubricant suitable for the application. The lubrication film 318 inhibits the transfer of vibrational energy, and thus heat, from the ultrasonic horn 316 to the static casing 310. The fluid channels 314 allow the flow of various types of fluid, including coolants, therapeutic agents, and osteoinductive agents, through the static casing 310.

Figure 4:
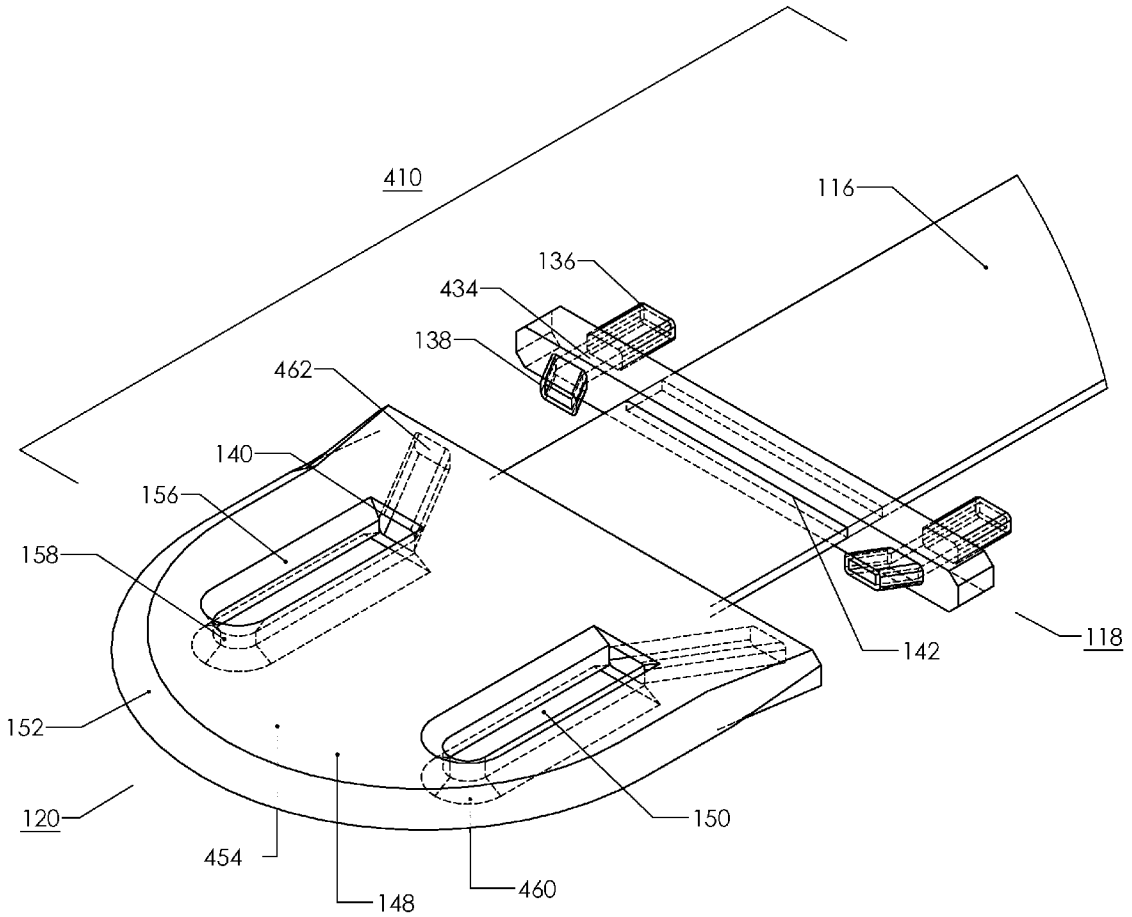
FIG. 4 is a close-up perspective view indicating many details of one embodiment of a cutting end assembly.

FIG. 4 is a close-up and exploded perspective view of one embodiment of a cutting end assembly 410. The cutting end assembly 410 comprises a cutting end 120, a flexible joint 118, and an opposite end of a static casing 114. An ultrasonic horn 116 comprises a first end and a second end, the second end coupled to the cutting end 120. The static casing 114 is better visualized in FIG. 1. At least a portion of the ultrasonic horn 116 is surrounded by the flexible joint 118, the flexible joint 118 separating the cutting end 120 from the opposite end of the static casing 114. The cutting end 120 comprises a plurality of inlets 462 and a plurality of discharge orifices 140. Each inlet 462 communicates with at least one of the discharge orifices 140. The cutting end 120 further comprises a blade edge 152, the blade edge 152 illustrated being a continuous arc that is sharpened along its entirety. The cutting end 120 is characterized in part by a top planar surface 148, the top planar surface 148 being defined by a plurality of openings 150.

Each opening 150 communicates with at least one of the discharge orifices 140. Each opening 150 extends the depth of the cutting end 120 from the top planar surface 148 to a bottom planar surface 454 of the cutting end 120. Each opening 150 is characterized in part by both a sloped top surface 156 and a sloped bottom surface 460. Both the sloped top surface 156 and the sloped bottom surface 460 originate from an interior edge 158, the interior edge 158 being positioned approximately along the median horizontal plane of the cutting end 120. The interior edge 158 extends substantially around the circumference of the opening 150. The sloped top surface 156, originating from the interior edge 158, extends substantially around the circumference of the opening 150 and slopes away from the interior edge 158 toward the top planar surface 148. The sloped bottom surface 460, originating from the interior edge 158, extends substantially around the circumference of the opening 150 and slopes away from the interior edge 158 toward the bottom planar surface 454.

The flexible joint 118 comprises a plurality of through-ports 434, a plurality of channel inserts 136, and a plurality of inlet connectors 138. The flexible joint 118 further comprises a passage 142, the passage 142 being substantially aligned with a sheathing slot 126 defining the static casing 114. The sheathing slot 126 and static casing 114 are better visualized in FIG. 1. At least a portion of the ultrasonic horn 116 passes through the passage 142. Each channel insert 136 communicates at one end with at least one of a plurality of fluid channels 130 defining the static casing 114. Each channel insert 136 communicates at an opposite end with one of the through-ports 434. Each inlet connector 138 communicates at one end with one of the through-ports 434 and communicates at an opposite end with one of the inlets 462. Communication between the fluid channels 130, channel inserts 136, through-ports 434, inlet connectors 138, inlets 462, and discharge orifices 140 allows fluid to flow continuously from its source toward the blade edge 152. In addition to facilitating the continuous flow of fluid from the fluid channels 130 to the inlets 462, the flexible joint 118 also reduces the transfer of vibrational energy from the cutting end 120 to the static casing 114.

Figure 5:
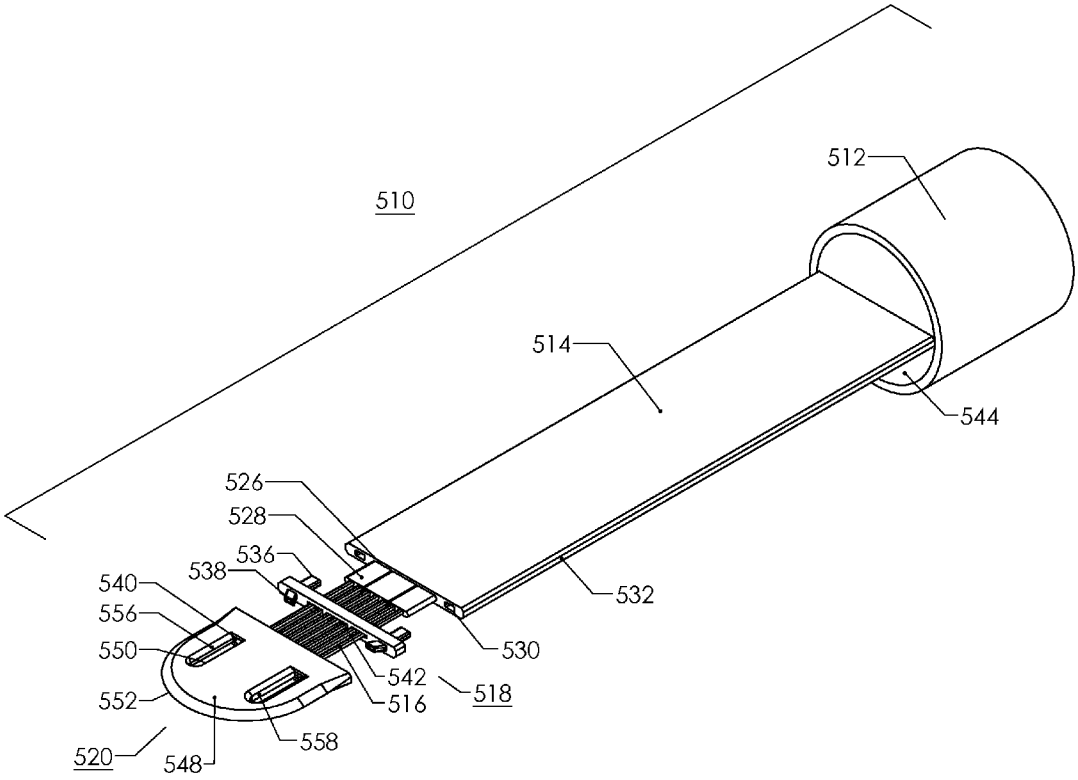
FIG. 5 is a perspective view of another embodiment showing a plurality of ultrasonic horns, a plurality of sheathing slots extending through a static casing, and a plurality of lubrication films separating the ultrasonic horns from the sheathing slots.

FIG. 5 is an exploded perspective view of another embodiment. An ultrasonic surgical device 510 comprises a housing 512, a static casing 514, a plurality of ultrasonic horns 516, a flexible joint 518, and a cutting end 520. The housing 512 contains components, such as a piezoelectric transducer and a transducer backing material, known to those skilled in the art to be related to the generation and propagation of ultrasonic vibrations to the cutting end 520. The piezoelectric transducer, which produces ultrasonic vibrations, is operatively coupled to the first end of each ultrasonic horn 516. Vibrations propagate along the main body of each ultrasonic horn 516 toward the second end of each ultrasonic horn 516, the second end of each ultrasonic horn being coupled to the cutting end 520. The static casing 514 sheaths the plurality of ultrasonic horns 516, each ultrasonic horn 516 being preferably positioned within a sheathing slot 526 located approximately along the central longitudinal axis of the static casing 514. It should be noted that the plurality of ultrasonic horns 516 may be sheathed individually within a sheathing slot 526 or the plurality of ultrasonic horns 516 may be sheathed collectively within a sheathing slot 526. Alternatively, groupings of the plurality of ultrasonic horns 516 may be sheathed within separate sheathing slots 526 so that, for example, some ultrasonic horns 516 are sheathed within one sheathing slot 526 while other ultrasonic horns 516 are sheathed within an adjacent sheathing slot 526. Each sheathing slot 526 and each ultrasonic horn 516 are separated from one another by at least one lubrication film 528. The lubrication film 528 reduces transfer of vibrational energy from the ultrasonic horn 516 and, thus, heat to the static casing 514. The static casing 514 and the cutting end 520 are separated by the flexible joint 518, which reduces the transfer of vibrational energy from the cutting end 520 to the static casing 514.

The static casing 514 comprises an attachment end 544 and an opposite end, the attachment end 544 adapted for coupling to the housing 512. The static casing 514 further comprises a plurality of fluid channels 530 which extend the length of the static casing 514. A plurality of longitudinal edges 532 further define the static casing 514, these longitudinal edges 532 being preferably rounded or filleted.

The flexible joint 518 is characterized in part by a plurality of channel inserts 536, a plurality of inlet connectors 538, and at least one passage 542. The passage 542 is substantially aligned with the sheathing slot 526 and allows at least a portion of at least one of the ultrasonic horns 516 to pass through the flexible joint 518. Better visualized in FIG. 6, the flexible joint further comprises a plurality of through-ports 634. Each channel insert 536 communicates with the fluid channel 530 of the static casing 514, allowing fluid to flow continuously from the fluid channel 530 through the through-port 634.

The cutting end 520 includes a plurality of inlets 662, a plurality of discharge orifices 540, and a plurality of openings 550. Each inlet connector 538 communicates with one of the inlets 662, each inlet 662 communicating with at least one of the discharge orifices 540. Each discharge orifice 540 communicates with at least one opening 550. Communication between the fluid channel 530, the channel insert 536, the through-port 634, the inlet connector 538, the inlet 662 and the discharge orifice 540 facilitates the continuous flow of fluid through the static casing 514, flexible joint 518, and to the cutting end 520. It is preferred that the flexible joint comprise both the channel inserts and the inlet connectors in order to facilitate continuous fluid flow. However, it should be noted that the flexible joint can comprise channel inserts but not inlet connectors, inlet connectors but not channel inserts, or neither channel inserts nor inlet connectors.

The cutting end 520 can be a blade tip adapted to cutting, ablating, abrading or otherwise transforming, for example, bone tissue. The cutting end 520 comprises a top planar surface 548 and a bottom planar surface 654. The bottom planar surface 654 is better visualized in FIG. 6. The cutting end 520 further includes at least one blade edge 552, the blade edge 552 preferably being a continuous, planar arc, and sharpened along its entirety. It should be noted, however, that the blade edge 552 can be adapted to have serrations or any other type of edge suitable for cutting, ablating, or otherwise transforming, for example, bone tissue. Each opening 550 extends through the depth of the cutting end 520 from the top planar surface 548 to the bottom planar surface 654. Each opening 550 is substantially circular and each is characterized in part by a sloped top surface 556 originating from an interior edge 558 situated approximately along the median horizontal plane of the cutting end 520. The sloped top surface 556 slopes up from the interior edge 558 and toward the top planar surface 548. Better visualized in FIG. 6, each opening 550 is further characterized by a sloped bottom surface 660, which originates from the interior edge 558 situated approximately along the median horizontal plane of the cutting end 520. The sloped bottom surface 660 slopes down from the interior edge 558 and toward the bottom planar surface 654.

Figure 6:
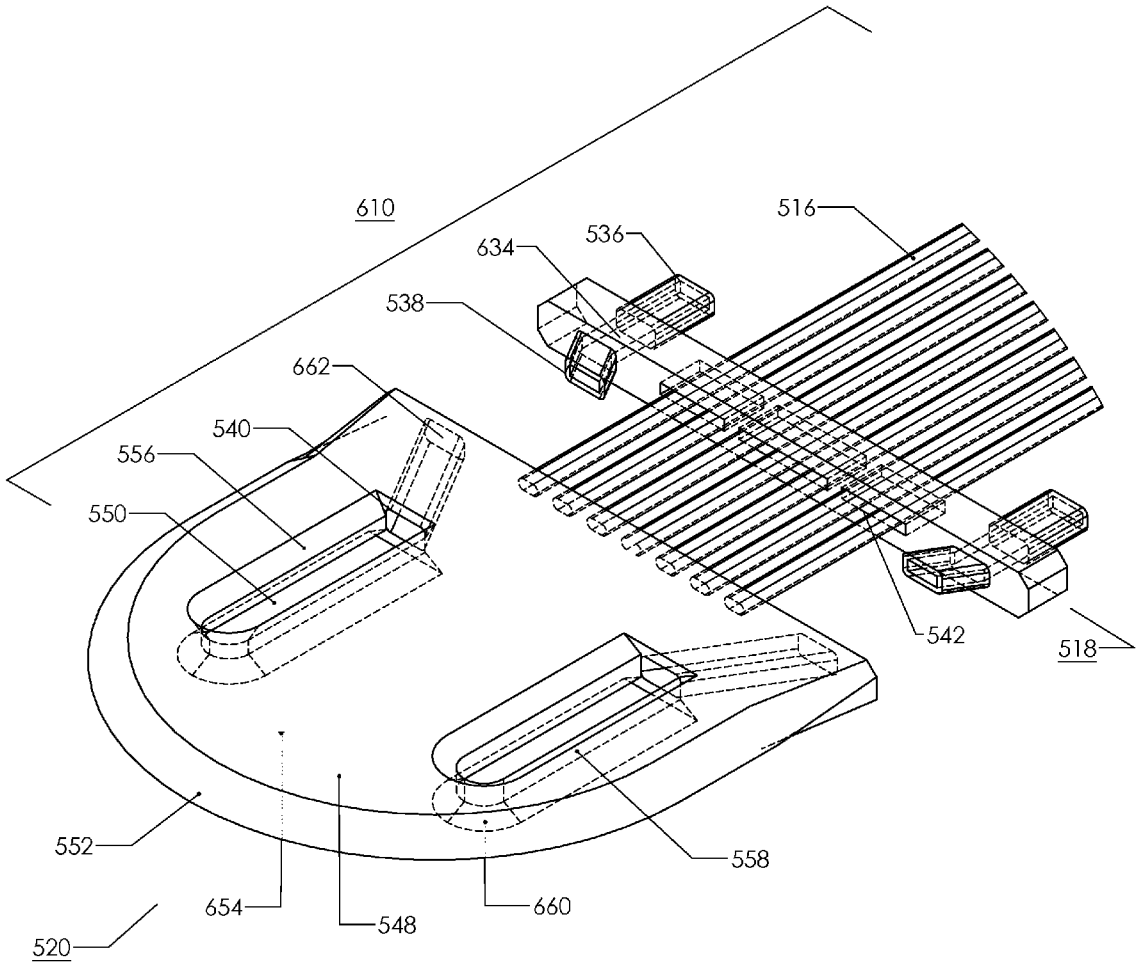
FIG. 6 is a close-up perspective view indicating many details of another embodiment of a cutting end assembly.

FIG. 6 is a close-up and exploded perspective view of one embodiment of a cutting end assembly 610. A plurality of ultrasonic horns 516 are attached to the cutting end 520. The cutting end 520 comprises a plurality of inlets 662 and a plurality of discharge orifices 540, each inlet 662 communicating with at least one of the discharge orifices 540. The cutting end 520 further comprises a blade edge 552, the blade edge 552 illustrated having a continuous arc that is sharpened along its entirety. The cutting end 520 is characterized in part by a top planar surface 548, the top planar surface 548 being defined by a plurality of openings 550. Each opening 550 communicates with at least one of the discharge orifices 540. A flexible joint 518 comprises a plurality of through-ports 634, a plurality of channel inserts 536, and a plurality of inlet connectors 538. The flexible joint 518 further comprises at least one passage 542, the passage being substantially aligned with a sheathing slot 526 defining a static casing 514. The sheathing slot 526 and static casing 514 are better visualized in FIG. 4. At least a portion of at least one of the ultrasonic horns 516 passes through the passage 542.

Each opening 550 extends the depth of the cutting end 520 from the top planar surface 548 to a bottom planar surface 654 of the cutting end 520. Each opening 550 is characterized in part by both a sloped top surface 556 and a sloped bottom surface 660. Both the sloped top surface 556 and the sloped bottom surface 660 originate from an interior edge 558, the interior edge 558 being positioned approximately along the median horizontal plane of the blade tip 546. The interior edge 558 extends substantially around the circumference of the opening 550. The sloped top surface 556, originating from the interior edge 558, extends substantially around the circumference of the opening 550 and slopes away from the interior edge 558 toward the top planar surface 548. The sloped bottom surface 660, originating from the interior edge 558, extends substantially around the circumference of the opening 550 and slopes away from the interior edge 558 toward the bottom planar surface 654.

Each channel insert 536 communicates at one end with one of the fluid channels 530 defining a static casing 514. The static casing 514 comprising the fluid channels 530 is better visualized in FIG. 5. Each channel insert 536 communicates at an opposite end with one of the through-ports 634. Each inlet connector 538 communicates at one end with one of the through-ports 634 and communicates at an opposite end with one of the inlets 562. Communication between the fluid channels 530, channel inserts 536, through-ports 634, inlet connectors 538, inlets 662, and discharge orifices 540 allows fluid to flow continuously from its source toward the blade edge 552. In addition to facilitating the continuous flow of fluid from the fluid channels 530 to the inlets 662, the flexible joint 518 also reduces the transfer of vibrational energy from the cutting end 520 to the static casing 514.

Figure 7:
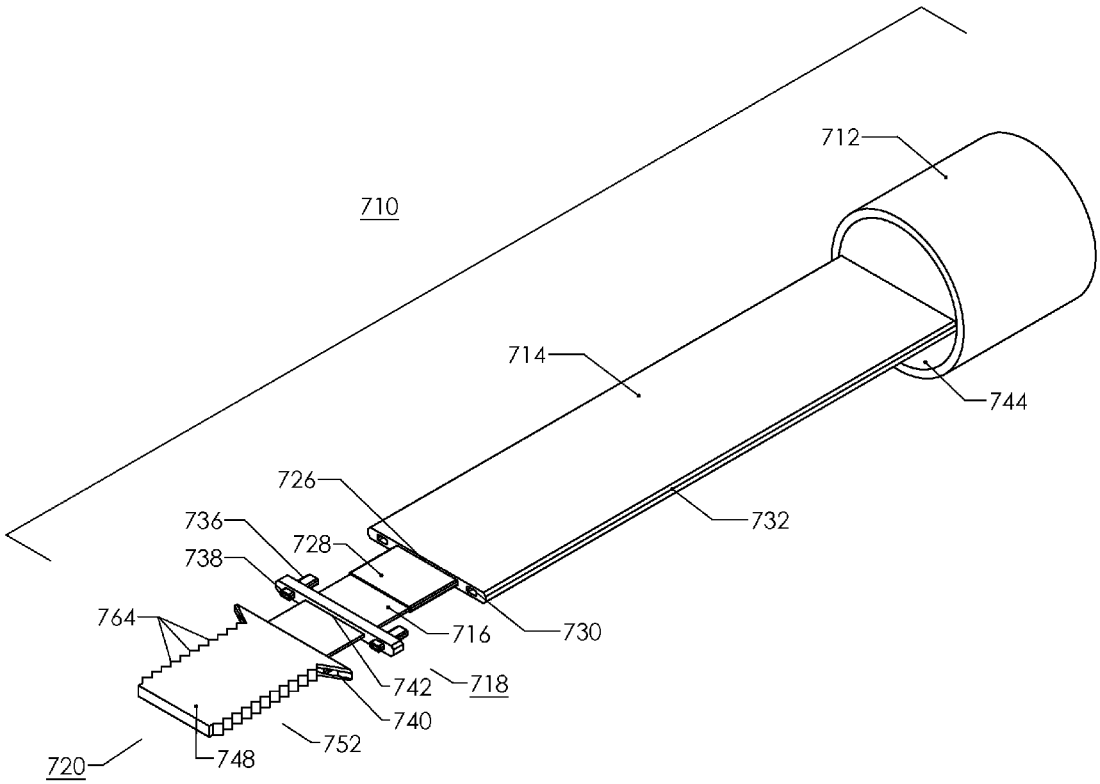
FIG. 7 is a perspective view of another embodiment of a cutting end having serrations.

FIG. 7 is an exploded perspective view of another embodiment. An ultrasonic surgical device 710 comprises a housing 712, a static casing 714, an ultrasonic horn 716, a flexible joint 718, and a cutting end 720. The housing 712 contains components, such as a piezoelectric transducer and a transducer backing material, known to those skilled in the art to be related to the generation and propagation of ultrasonic vibrations to the cutting end 720. The piezoelectric transducer, which produces ultrasonic vibrations, is operatively coupled to the first end of the ultrasonic horn 716. Vibrations propagate along the main body of the ultrasonic horn 716 toward the second end of each ultrasonic horn 716, the second end being coupled to the cutting end 720. The static casing 714 sheaths the ultrasonic horn 716, the ultrasonic horn 716 being preferably positioned within a sheathing slot 726 located approximately along the central longitudinal axis of the static casing 714. The sheathing slot 726 and the ultrasonic horn 716 are separated from one another by at least one lubrication film 728. The lubrication film 728 reduces transfer of vibrational energy from the ultrasonic horn 716 and, thus, heat to the static casing 714. The static casing 714 and the cutting end 720 are separated by the flexible joint 718, which reduces the transfer of vibrational energy from the cutting end 720 to the static casing 714.

The static casing 714 comprises an attachment end 744 and an opposite end, the attachment end 744 adapted for coupling to the housing 712. The static casing 714 further comprises a plurality of fluid channels 730 which extend the length of the static casing 714. A plurality of longitudinal edges 732 further define the static casing 714, these longitudinal edges 732 being preferably rounded or filleted. The flexible joint 718 is characterized in part by a plurality of channel inserts 736, a plurality of through-ports 834, a plurality of inlet connectors 738, and at least one passage 742. The passage 742, which is substantially aligned with the sheathing slot 726, allows at least a portion of the ultrasonic horn 716 to pass through the flexible joint 718. Each channel insert 736 communicates with the fluid channel 730 of the static casing 714, allowing fluid to flow continuously from the fluid channel 730 through the through-port 834. The cutting end 720 includes a plurality of inlets 862 and a plurality of discharge orifices 740. The through-ports 834 and inlets 862 are better visualized in FIG. 8. Each inlet connector 738 communicates with one of the inlets 862 and each inlet 862 communicates with at least one of the discharge orifices 740. Communication between the fluid channel 730, the channel insert 736, the through-port 834, the inlet connector 738, the inlet 862 and the discharge orifice 740 facilitates the continuous flow of fluid through the static casing 714, flexible joint 718, and to the cutting end 720. It is preferred that the flexible joint 718 comprise both the channel inserts 736 and the inlet connectors 738 in order to facilitate continuous fluid flow. However, it should be noted that the flexible joint 718 can comprise channel inserts 736 but not inlet connectors 738, inlet connectors 738 but not channel inserts 736, or neither channel inserts 736 nor inlet connectors 738.

The cutting end 720 can be a blade tip adapted to cutting, ablating, abrading or otherwise transforming, for example, bone tissue. The cutting end 720 comprises a top planar surface 748 and a bottom planar surface 854. The bottom planar surface 854 is better visualized in FIG. 8. The cutting end 720 further includes at least one blade edge 752, the blade edge 752 in this embodiment preferably having serrations along at least a portion of the blade edge 752. These serrations comprise a plurality of blade teeth 764. It should be noted, however, that the blade edge 752 can be adapted to have any other type of edge suitable for cutting, ablating, or otherwise transforming, for example, bone tissue.

Figure 8:
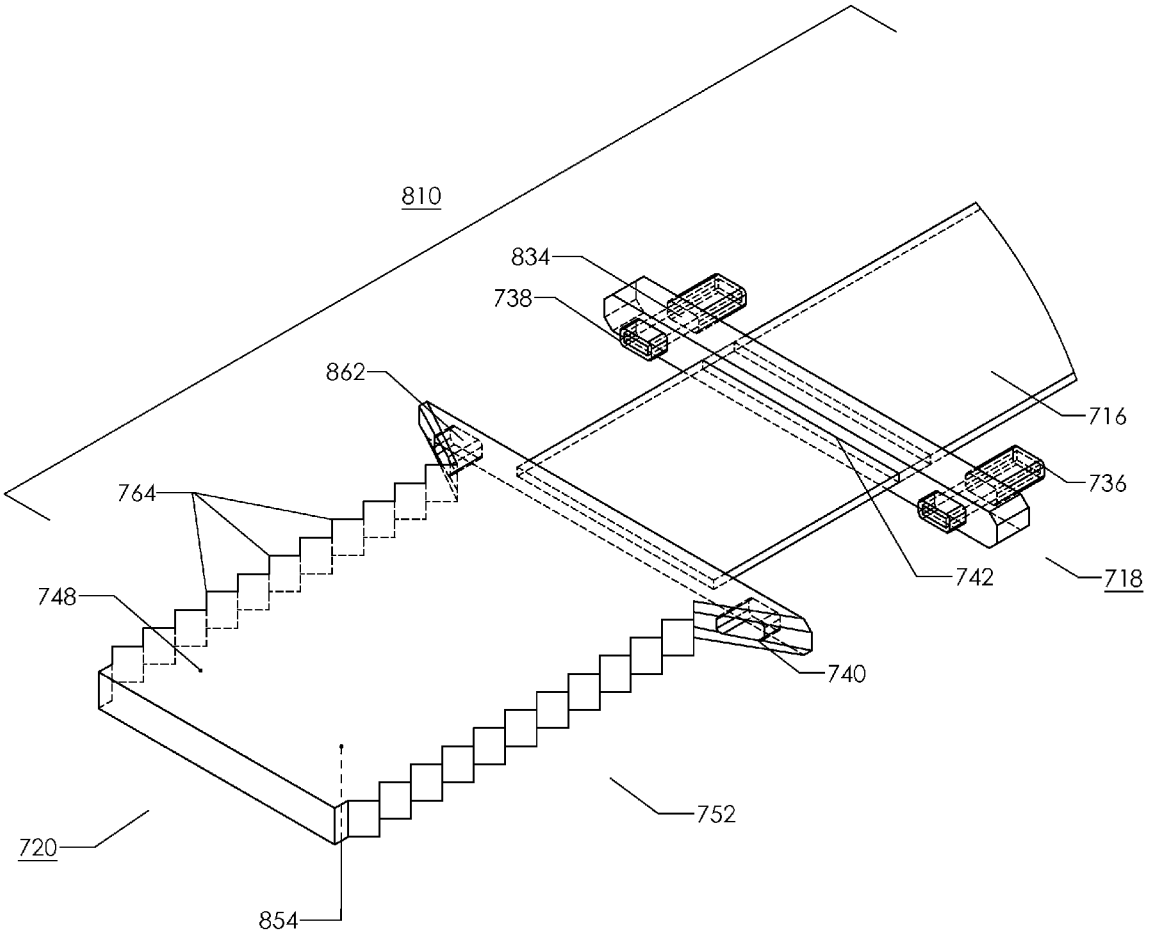
FIG. 8 is a close-up perspective view indicating many details of one embodiment of a cutting end assembly that includes serrations.

FIG. 8 is a close-up and exploded perspective view of one embodiment of a cutting end assembly 810. An ultrasonic horn 716 is attached to the cutting end 720. The cutting end 720 comprises a plurality of inlets 862 and a plurality of discharge orifices 740, each inlet 862 communicating with at least one of the discharge orifices 740. The cutting end 720 further comprises a blade edge 752, the blade edge 752 illustrated having serrations along at least a portion of the blade edge 752. The cutting end 720 is characterized in part by a top planar surface 748 and a bottom planar surface 854. A flexible joint 718 comprises a plurality of through-ports 834, a plurality of channel inserts 736, and a plurality of inlet connectors 738. The flexible joint 718 further comprises a passage 742, the passage 742 being substantially aligned with a sheathing slot 726 defining a static casing 714. The sheathing slot 726 and static casing 714 are better visualized in FIG. 7. At least a portion of the ultrasonic horn 716 passes through the passage 742.

Each channel insert 736 communicates at one end with one of the fluid channels 730 defining a static casing 714. Each channel insert 736 communicates at an opposite end with one of the through-ports 834. Each inlet connector 738 communicates at one end with one of the through-ports 834 and communicates at an opposite end with one of the inlets 862. Communication between the fluid channels 730, channel inserts 736, through-ports 834, inlet connectors 738, inlets 862, and discharge orifices 740 allows fluid to flow continuously from its source toward the blade edge 752. In addition to facilitating the continuous flow of fluid from the fluid channels 730 to the inlets 862, the flexible joint 718 also reduces the transfer of vibrational energy from cutting end 720 to the static casing 714.

Figure 9:
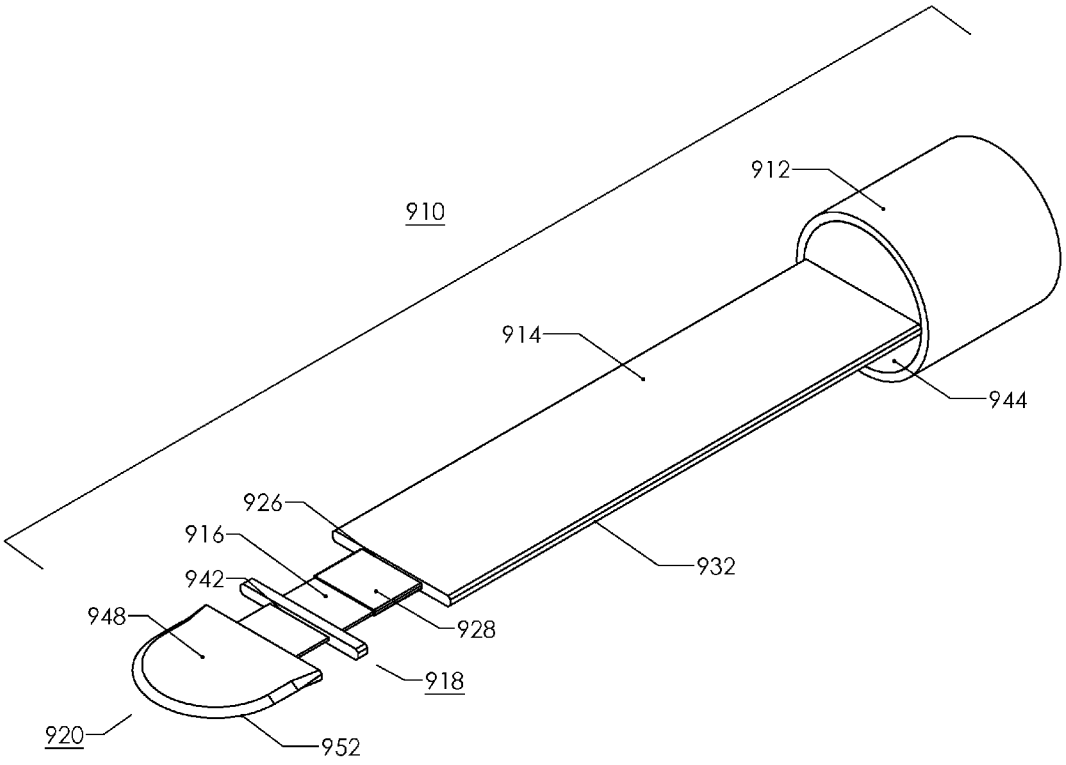
FIG. 9 is an exploded perspective view indicating many components of another embodiment.

FIG. 9 is an exploded perspective view of another embodiment for an ultrasonic surgical device. The ultrasonic surgical device 910 comprises a housing 912, a static casing 914, an ultrasonic horn 916, a flexible joint 918, and a cutting end 920. The housing 912 contains components, such as a piezoelectric transducer and a transducer backing material, known to those skilled in the art to be related to the generation and propagation of ultrasonic vibrations to the cutting end 920. The piezoelectric transducer, which produces ultrasonic vibrations, is operatively coupled to the first end of the ultrasonic horn 916. Vibrations propagate along the main body of the ultrasonic horn 916 toward the second end of each ultrasonic horn 916, the second end being coupled to the cutting end 920. The static casing 914 sheaths the ultrasonic horn 916, the ultrasonic horn 916 being preferably positioned within a sheathing slot 926 located approximately along the central longitudinal axis of the static casing 914. The sheathing slot 926 and the ultrasonic horn 916 are separated from one another by at least one lubrication film 928. The lubrication film 928 reduces transfer of vibrational energy from the ultrasonic horn 916 and, thus, heat to the static casing 914. The static casing 914 and the cutting end 920 are separated by the flexible joint 918, which reduces the transfer of vibrational energy from the cutting end 920 to the static casing 914.

The static casing 914 comprises an attachment end 944 and an opposite end, the attachment end 944 adapted for coupling to the housing 912. A plurality of longitudinal edges 932 further define the static casing 914, these longitudinal edges 932 being preferably rounded or filleted. The flexible joint 918 is characterized in part by at least one passage 942. The passage 942, which is substantially aligned with the sheathing slot 926, allows at least a portion of the ultrasonic horn 916 to pass through the flexible joint 918. The cutting end 920 can be a blade tip adapted to cutting, ablating, or otherwise transforming, for example, bone tissue. The cutting end 920 comprises a top planar surface 948 and a bottom planar surface. The cutting end 920 further includes at least one blade edge 952.

While specific embodiments of the present invention and applications of the invention have been described herein, it will be apparent to those of ordinary skill in the art that many variations on the embodiments and applications described herein are possible without departing from the scope of the invention described and claimed herein. It should be understood that while certain embodiments of the invention have been shown and described, the invention is not to be limited to the specific embodiments described and illustrated.

What is claimed is:

1. An ultrasonic bone cutting device, comprising:

a housing, said housing containing a source of ultrasonic vibrations;

an ultrasonic horn, said ultrasonic horn having a first end, an elongated main body, and a second end, said first end coupled to said source of ultrasonic vibrations, said second end coupled to a cutting end, said cutting end comprising top planar surface and opposing bottom planar surface, a distal continuous blade edge without interrupting openings connecting the top planar surface to the bottom planar surface, a plurality of spaced apart through discharge orifices extending through a depth of the cutting end through the top and bottom planar surfaces and spaced apart from the continuous blade edge, and a proximal edge connecting the top planar surface to the bottom planar surface and including a plurality of spaced apart inlets in fluid communication with the through discharge orifices;

a static casing formed from a rigid biocompatible material, said static casing having an attachment end, an opposite end, and a sheathing slot, said static casing defining a plurality of spaced apart fluid channels, said fluid channels extending a length of said static casing, said attachment end configured to be coupled to said housing, said sheathing slot extending the length of said static casing, said sheathing slot sheathing a length of said elongated main body; said static casing having a height and a width profile equal to a height and a width profile of said cutting end;

a solid lubrication film adhered to at least one of an external surface of the elongated main body and an internal surface of the sheathing slot, said solid lubrication film separating said sheathing slot from said elongated main body;

a flexible joint formed from a viscoelastic material, said flexible joint positioned between said opposite end of said static casing and said proximal edge of said cutting end, said flexible joint having a height and a width profile equal to the height and the width profile of said cutting end, said flexible joint having a proximal end and a distal end, said proximal end defining a plurality of spaced apart channel inserts and said distal end defining a plurality of spaced apart inlet connectors in fluid communication with said channel inserts, such that a through-port extends through each of the channel inserts and the corresponding inlet connector, and said flexible joint defining a passage extending therethrough, said through-ports are in fluid communication with said spaced apart fluid channels and said spaced apart inlets, said passage substantially aligned with said sheathing slot, a portion of said elongated main body passing through said passage; and whereby fluid from at least one reservoir flows through said fluid channels, through said through-ports, and out of said through discharge orifices, said fluid cools said ultrasonic horn, said static casing, said flexible joint, and said cutting end, said lubrication film reduces generation of heat between said sheathing slot and said elongated main body, said static casing configured to reduces transfer of heat generated by the ultrasonic vibrations along the length of said elongated main body to neighboring biological tissues, said flexible joint reduces transfer of the ultrasonic vibrations from said cutting end to said static casing, the equal height and width profiles of said static casing, said flexible joint, and said cutting end configured to facilitate effective penetration into and cutting of large cross-sections of biological tissue.

2. The ultrasonic bone cutting device of claim 1, wherein said solid lubrication film coats a portion of at least one of said main body and said sheathing slot.

3. The ultrasonic bone cutting device of claim 1, wherein said blade edge is configured for ablating.

4. The ultrasonic bone cutting device of claim 1, wherein said blade edge is configured for abrading.

5. The ultrasonic bone cutting device of claim 1, wherein a portion of an outer surface of at least one of said static casing and said cutting end is coated with a lubricant.

6. The ultrasonic bone cutting device of claim 1, wherein said fluid channels are individually operable such that each of said fluid channels configured to deliver at least one of separate fluids, separate fluid volumes, or separate fluid pressures to the cutting end.

* * * * *